(12) United States Patent
Dey et al.

(10) Patent No.: US 7,276,258 B2
(45) Date of Patent: Oct. 2, 2007

(54) HERBAL EXTRACT AND COMPOUND LUPINOSIDE AND ITS ANALOGUES AS ANTI-DIABETIC TYPE II DRUGS FROM PLANT PUERARIA TUBEROSA

(75) Inventors: Debleena Dey, Kolkatta (IN); Swapan Kumar Mandal, Kolkatta (IN); Mohua Mukherjee, Kolkatta (IN); Bikash Chandra Pal, Kolkatta (IN); Tanushree Biswas, Kolkatta (IN); Malabika Datta, Kolkatta (IN); Sib Sankar Roy, Kolkatta (IN); Arun Bandyopadhyay, Kolkatta (IN); Samir Bhattacharya, Kolkatta (IN); Bir Bhanu Giri, West Bengal (IN); Santu Bandopadhyay, Kolkatta (IN); Aditya Konar, Kolkatta (IN)

(73) Assignee: Council of Scientific & Industrial Research, New Delhi (IN)

( * ) Notice: Subject to any disclaimer, the term of this patent is extended or adjusted under 35 U.S.C. 154(b) by 26 days.

(21) Appl. No.: 10/809,645

(22) Filed: Mar. 25, 2004

(65) Prior Publication Data

US 2005/0153000 A1 Jul. 14, 2005

Related U.S. Application Data

(60) Provisional application No. 60/535,332, filed on Jan. 9, 2004.

(51) Int. Cl.
*A01N 65/00* (2006.01)
*A61N 43/04* (2006.01)
*A61K 31/70* (2006.01)

(52) U.S. Cl. .................. 424/757; 514/25; 514/866

(58) Field of Classification Search ................ 424/725; 514/866, 783, 24, 25
See application file for complete search history.

(56) References Cited

U.S. PATENT DOCUMENTS 5,773,004 A * 6/1998 Takahashi

OTHER PUBLICATIONS

Davies M J et al., Diabetic Medicine (May 2004), 21(5): 403-414. Prevention of Type 2 diabetes mellitus. A review of the evidence and its application in a UK setting.*
Sturis, J et al., American J of Physiology (1995), 269(4Pt 1): E786-92. Prevention of diabetes does not completely prevent insulin secretion defects in the ZDF rat.*
Shukla, S. International Journal of Pharmacognosy (1995), 33(4): 324-3293 Toxicology studies of *Pueraria tuberosa*, a potent antifertility plant. Abstract.*
Friedman, J. E. et al. American Journal of Physiology (1991), 261(6): 74-80. Altered expression of muscle glucose transporter GLUT-4 in diabetic fatty Zucker rats (ZDF/Drt-fa).*

* cited by examiner

*Primary Examiner*—Michele Flood
(74) *Attorney, Agent, or Firm*—Madan, Mossman & Sriram, P.C.

(57) ABSTRACT

The present invention relates to a method of preventing and/or treating diabetes type 2, also, it relates to a method of augmenting Glut4 phosphorylation and Glut4 translocation to a target cell membrane to enhance insulin signal in a signal transduction pathway; further, it relates to a simplified and inexpensive process of obtaining extract and thereafter selectively, its active n-butanol fraction and active molecule Lupinoside PA ($LPA_4$), useful in preventing and/or treating diabetes type 2; and lastly, a pharmaceutical composition thereof.

7 Claims, 6 Drawing Sheets

Figure 1C:
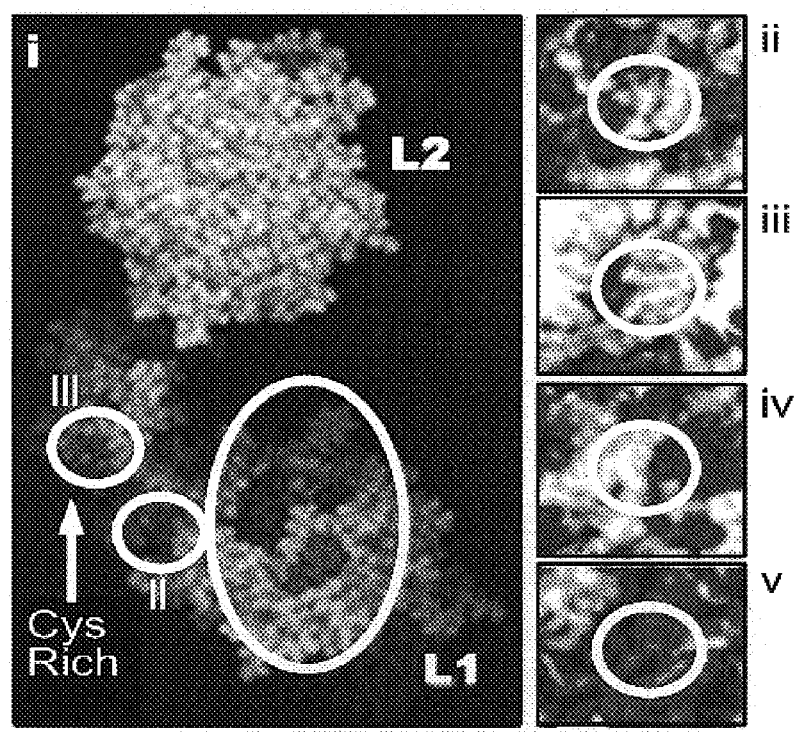

(3 of 6 Drawing Sheet(s) Filed in Color)

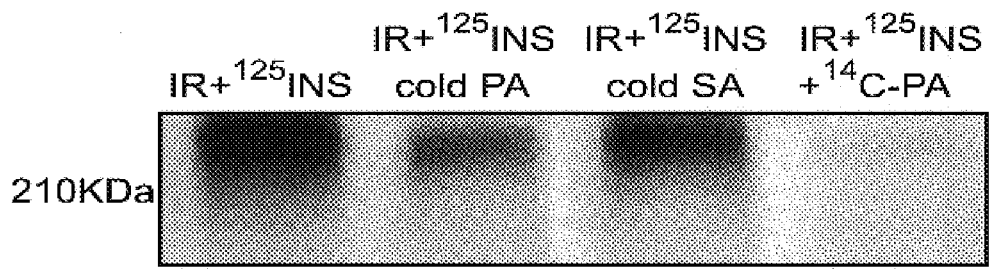
*FIG. 1A*
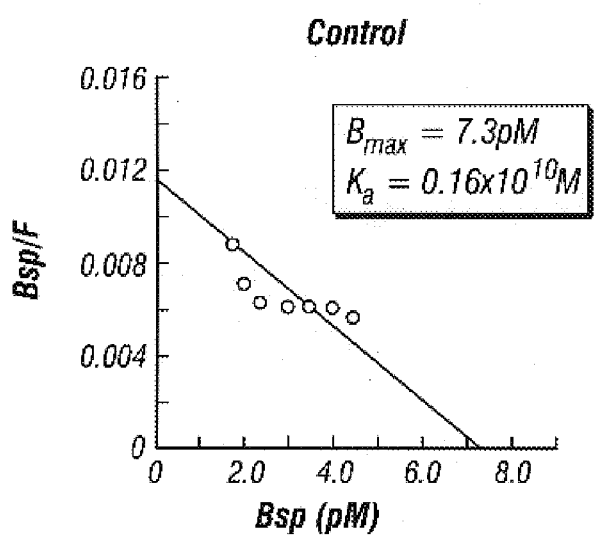
*FIG. 1B*
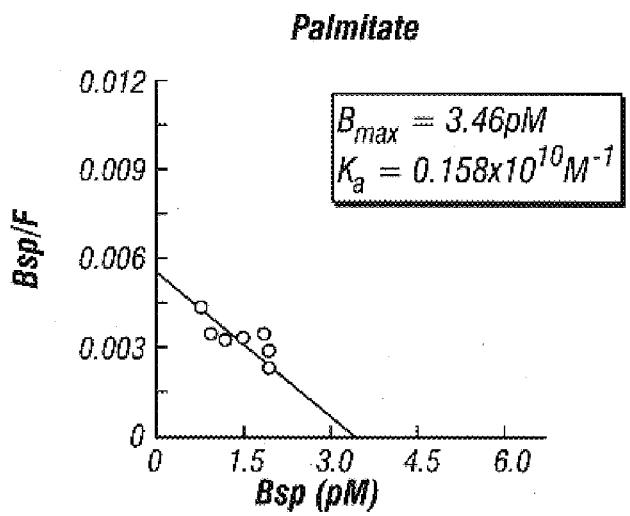

Lupinoside PA$_4$

Structure of Lupinoside PA$_4$

HERBAL EXTRACT AND COMPOUND LUPINOSIDE AND ITS ANALOGUES AS ANTI-DIABETIC TYPE II DRUGS FROM PLANT PUERARIA TUBEROSA

RELATED APPLICATIONS

This application claims priority from U.S. Provisional Patent Application Ser. No. 60/535,332 filed on Jan. 9, 2004.

BACKGROUND OF THE INVENTION

1. Field of Invention

The present invention relates to a method of preventing and/or treating diabetes type 2, also, it relates to a method of augmenting Glut4 phosphorylation and Glut4 translocation to a target cell membrane to enhance insulin signal in a signal transduction pathway; further, it relates to a simplified and inexpensive process of obtaining extract and thereafter selectively, its active n-butanol fraction and active molecule Lupinoside PA ($LPA_4$), useful in preventing and/or treating diabetes type 2; and lastly, a pharmaceutical composition thereof.

2. Background of the Present Invention

Type 2 insulin-resistant diabetes mellitus, an insidious disease, accounts for more than 95% of diabetic cases. This heterogeneous disorder is increasing in epidemic proportions, its world wide frequency is expected to grow more than six percent per anum[1,2]. The disease is primarily expressed in the form of hyperglycemia due to defects in glucose disposal into skeletal muscle, fat and liver as they become less responsive or resistant to insulin[3,4]. Large number of evidences has been accumulated that hold free fatty acids (FFAs) responsible for insulin inaction. Elevated FFAs in circulation is associated with impaired insulin function and is commonly linked with obesity and type 2 diabetes[5-7]. Rising of plasma FFA concentrations through lipid infusion causes insulin resistance in rat and human skeletal muscle[7-9]. Incubation of isolated muscle strips or cultured muscle cells with FFAs or lipoprotein lipase expression in skeletal muscle reduces insulin-mediated glucose uptake[6-12]. These reports suggest that greater deposition of lipid in insulin sensitive tissues promotes insulin inaction and resistance. FFA induced impairment of insulin activity appears to be associated with insulin signaling defects. Lowering of glucose transport by FFA is linked to inhibition of insulin-stimulated IRS-1 phosphorylation and IRS-1 associated phosphatidylinositol-3-phosphate kinase (PI3K) activation[13-15]. Thiazolidinedione (TZD) treatment reduces circulating FFAs that oppose insulin actions in target tissues improving insulin activity[16-18]. By inducing the glycerol kinase gene expression in adipocytes through the activation of PPARγ, TZD augments glycerol incorporation into triglyceride thus reduces FFA secretion from the adipocyte and that helps insulin sensitizations[19].

OBJECTS OF THE PRESENT INVENTION

The main object of the present invention is to develop a method of preventing and/or treating diabetes type 2.

Another main object of the present invention is to develop a method of augmenting Glut4 phosphorylation and Glut4 translocation to a target cell membrane to enhance insulin signal in a signal transduction pathway.

Yet another object of the present invention is to develop a simplified and inexpensive process of obtaining extract and thereafter selectively, its active n-butanol fraction and active molecule Lupinoside PA ($LPA_4$), useful in preventing and/or treating diabetes type 2.

Still another object of the present invention is to develop a pharmaceutical composition for preventing and/or treating diabetes type 2.

SUMMARY OF THE PRESENT INVENTION

The present invention relates to a method of preventing and/or treating diabetes type 2, also, it relates to a method of augmenting Glut4 phosphorylation and Glut4 translocation to a target cell membrane to enhance insulin signal in a signal transduction pathway; further, it relates to a simplified and inexpensive process of obtaining extract and thereafter selectively, its active n-butanol fraction and active molecule Lupinoside PA ($LPA_4$), useful in preventing and/or treating diabetes type 2; and lastly, a pharmaceutical composition thereof.

DETAILED DESCRIPTION OF THE PREFERRED EMBODIMENT

Accordingly, the present invention relates to a method of preventing and/or treating diabetes type 2, also, it relates to a method of augmenting Glut4 phosphorylation and Glut4 translocation to a target cell membrane to enhance insulin signal in a signal transduction pathway; further, it relates to a simplified and inexpensive process of obtaining extract and thereafter selectively, its active n-butanol fraction and active molecule Lupinoside PA ($LPA_4$), useful in preventing and/or treating diabetes type 2; and lastly, a pharmaceutical composition thereof.

In still another embodiment of the present invention, wherein the invention relates to a method of preventing and/or treating diabetes type 2 in a subject in need thereof, said method comprising step of administering pharmaceutically effective amount of an extract of plant *Pueraria tuberosa* or butanol fraction of the extract or Lupinoside A4 (LPA4, optionally along with additive(s) to the subject.

In still another embodiment of the present invention, wherein the subject is an animal.

In still another embodiment of the present invention, wherein the subject is a human being.

In still another embodiment of the present invention, wherein the fraction is administered at the concentration ranging between 1 to 40 mg/kg body weight.

In still another embodiment of the present invention, wherein the invention relates to A method as claimed in claim 1, wherein the Lupinoside is administered at the concentration ranging between 1 to 40 mg/kg body weight.

In still another embodiment of the present invention, wherein the invention relates to A method as claimed in claim 1, wherein the administration route is selected from a group comprising orally, intravenously, intramuscularly, and subcutaneously.

In still another embodiment of the present invention, wherein the invention relates to a pharmaceutical composition useful in preventing and/or treating diabetes type 2, said composition comprising an extract of plant *Pueraria tuberosa* or butanol fraction of the extract or Lupinoside A4 (LPA4), and additive(s).

In still another embodiment of the present invention, wherein the additive is selected from a group comprising nutrients such as proteins, carbohydrates, sugars, talc, magnesium stearate, cellulose, calcium carbonate, starch, gelatin paste, pharmaceutically acceptable carrier, excipients, diluent and, solvent.

In still another embodiment of the present invention, wherein the extract is obtained from root of the plant.

In still another embodiment of the present invention, wherein the fraction is of concentration ranging between 1 to 40 mg/kg body weight.

In still another embodiment of the present invention, wherein the Lupinoside is of concentration ranging between 1 to 40 mg/kg body weight.

In still another embodiment of the present invention, wherein the composition is in a form selected from a group comprising capsule, syrup, concentrate, powder, and granules.

In still another embodiment of the present invention, wherein the extract is an aqueous extract.

In still another embodiment of the present invention, wherein the invention relates to a method of augmenting Glut4 phosphorylation and Glut4 translocation to a target cell membrane to enhance insulin signal in a signal transduction pathway in a subject in need thereof, said method comprising administering pharmaceutically effective amount of an extract of plant *Pueraria tuberosa* or butanol fraction of the extract or Lupinoside A4 (LPA4), optionally along with additive(s) to the subject.

In still another embodiment of the present invention, wherein the additive is selected from a group comprising nutrients such as proteins, carbohydrates, sugars, talc, magnesium stearate, cellulose, calcium carbonate, starch, gelatin paste, pharmaceutically acceptable carrier, excipients, diluent and, solvent.

In still another embodiment of the present invention, wherein the fraction is administered at the concentration ranging between 1 to 40 mg/kg body weight.

In still another embodiment of the present invention, wherein the Lupinoside is administered at the concentration ranging between 1 to 40 mg/kg body weight.

In still another embodiment of the present invention, wherein the method helps prevent/treat type 2 diabetes.

In still another embodiment of the present invention, wherein the method shows increase in glucose uptake by the cells.

In still another embodiment of the present invention, wherein the method is non-toxic to the cells.

In still another embodiment of the present invention, wherein the translocation is from cytosol to membrane of the insulin response cells.

In still another embodiment of the present invention, wherein the Lupinoside A4 ($LP_4$) prevents palmitate induced defects on insulin signaling.

In still another embodiment of the present invention, wherein the Lupinoside A4 ($LP_4$) allows insulin to stimulate IR-beta and Akt phosphorylation.

In still another embodiment of the present invention, wherein the invention relates to a simplified and inexpensive process of obtaining extract and thereafter selectively, its active n-butanol fraction and active molecule Lupinoside PA ($LPA_4$), useful in preventing and/or treating diabetes type 2, said process comprising steps of:

cutting the plant parts into small parts, extracting the cut parts with methanol and water, partitioning the methanol and water extract between ethyl acetate and water, extracting the aqueous layer further with n-butanol to obtain butanol fraction, and subjecting the n-butanol fraction to chromatography with water and methanol as eluent to obtain Lupinoside $PA_4$ ($LPA_4$).

In still another embodiment of the present invention, wherein the plant part is root.

In still another embodiment of the present invention, wherein the solvent is selected from a group comprising methanol, and water.

In still another embodiment of the present invention, wherein the water and methanol are in the ratio of about 1:1.

In still another embodiment of the present invention, wherein the chromatography is column chromatography.

The decrease in insulin sensitivity to target tissues or insulin resistance leads to diabetes type 2, a disease now reaching to epidemic proportions in industrialized societies. It is still unclear how insulin loses its sensitivity. A large number of evidences made free fatty acids (FFAs) responsible for insulin resistance. We have demonstrated that palmitate, one of the FFAs, interfered with insulin binding to 210 kDa receptor protein from 3T3L1 adipocyte cell membrane. Palmitate did not alter affinity of insulin binding as Ka remains unchanged, but it drastically reduced insulin occupation of receptor from Bmax 7.3 pM (insulin) to 3.46 pM (insulin plus palmitate). Inhibition of interaction of insulin with insulin receptor (IR) by palmitate coincided with the reduction of IRβ tyrosine phosphorylation, a critical target cell response followed by insulin-IR complex. We then examined insulin stimulated downstream signals, which are consequently phosphorylated following IRβ tyrosine phosphorylation. A 24 h incubation of 3T3L1 cells with palmitate affected about two-fold decrease of insulin-augmented IRS 1, PI3 Kinase and Akt phosphorylation and completely blocked insulin-induced Glut4 translocation. All these indicate downing of insulin signals by palmitate and that causes insulin inaction. Lupinoside A4 ($LPA_4$), isolated from a plant root, prevented palmitate-induced defects on insulin signaling. $LPA_4$ co-incubation with palmitate allowed insulin to stimulate IRβ and Akt phosphorylation, and insulin-induced Glut4 translocation. Hence, $LPA_4$ shows a promise for its use as a therapeutic agent in insulin resistance and diabetes type 2.

Figure 1D:
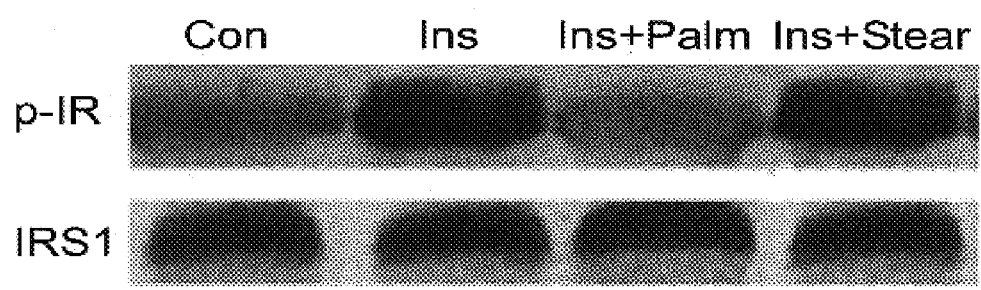

These reports drive our attention towards FFAs as the principal compound causing insulin resistance and diabetes type 2. Earlier reports indicated that among the FFAs, palmitate is the most potent inhibitor of insulin activity [12,20-23], but the question confronting us is how it imposes such defects. A 24 h pre-treatment of 3T3L1 adipocytes with palmitate, myristate, butyrate, caprylate, stearate, laureate and linoleate separately followed by 30 min incubation with insulin and then determination of $^3$H-2deoxyglucose (2-DOG) uptake showed that palmitate could be singled out as the most potent inhibitor (data not shown). This led us to search for the underlying mechanisms responsible for palmitate-induced inhibition of insulin stimulated glucose uptake. Palmitate incubated adipocytes were lysed, membranes were isolated, solubilised, subjected to non-denaturing SDS-PAGE then subjected to autoradiography. $^{125}$I-insulin bound protein could be located at 210 kDa region of the gel that corroborates earlier reports of detergent-solubilised insulin receptor under non-denaturing conditions with 3T3-L1 adipocytes[24-26]. FIG. 1a shows that palmitate effectively reduced insulin binding to the receptor. Palmitate binding or palmitoylation of IR, as reported with β-adrenergic receptor[27-29], did not alter the affinity but effected two-fold decrease in receptor occupation, $B_{max}$ was reduced from 7.3 to 3.46 pM (FIG. 1b). Since $^{125}$I-insulin binding to the receptor could not be reduced by stearate or myristate (data not shown), we presume this to be a specific palmitate effect. Interestingly, radiolabelled palmitate binds to similar molecular size protein (1a) suggesting palmitoylation of IR. With the help of a model, the logic behind this postulation is explained in FIG. 1c. In order to identify the probable site for palmitoylation, 3-D structure of the first three domains of rat insulin receptor was homology modeled based on the recently determined crystal structure of the type-1 insulin-like growth factor receptor[30]. Alanine scanning mutagenesis results strongly suggest that this area on the insulin receptor (within the cyan ring in FIG. 1c) is the most probable site for insulin binding[31]. The lack of consensus amino acid sequence[27] implies that palmitoylation preference is determined by the 3-D structure and it would be favored by a positively charged and/or neutral surface. The calculation of surface electrostatic potential of the modeled structure, solvent accessibility and proximity measurement of the cysteine residues have helped us to identify two potential pairs of Cys residues (Cys-8 & Cys-26 and Cys-266 & Cys-274) for palmitoylation out of 16 such pairs in the L1-Cys rich-L2 regions of the IR. Since mere association of palmitate with IR does not imply biological relevance, we studied palmitate interference on insulin stimulated signals to demonstrate the functional significance correlated with its binding. We first observed phosphorylation of insulin receptor β (IRβ) by incubating 3T3L1 cells without or with palmitate for 24h, followed by insulin incubation. Insulin-stimulated phosphorylation of IRβ was dramatically reduced by palmitate while stearate did not exhibit such inhibition (FIG. 1d). These results suggest palmitate association or palmitoylation of the receptor has physiological relevance since IRβ phosphorylation is a critical response from insulin target cell.

Figure 2A:
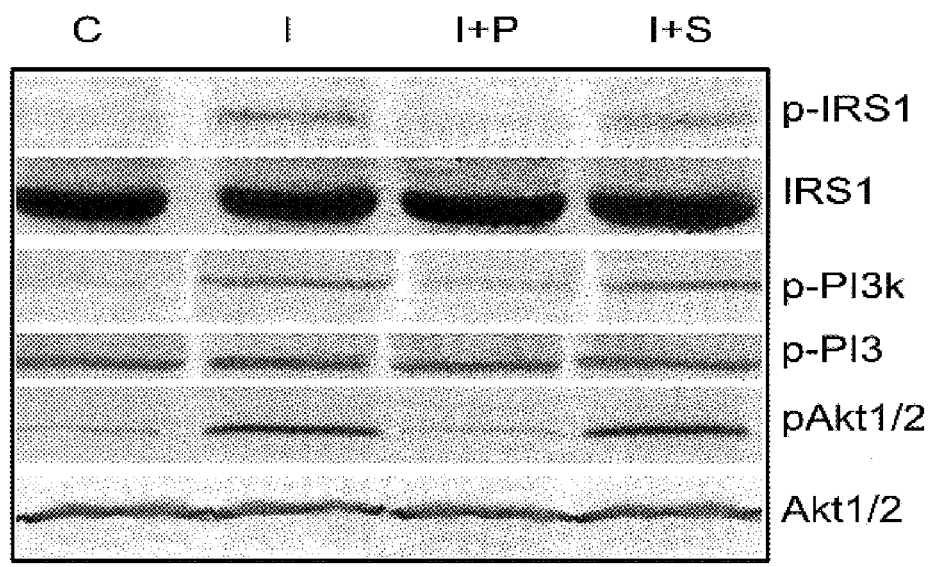
Figure 2B:
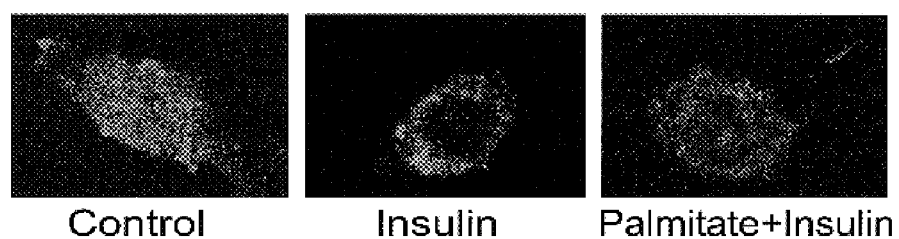

To have further evidence, we examined insulin augmented downstream signals, which get consequently phosphorylated following receptor tyrosine kinase phosphorylation. Using phospho-specific antibodies, we found that insulin stimulation of IRS-1 phosphorylation and PI3K activity was significantly inhibited by palmitate. Palmitate also reduced insulin stimulation of other downstream molecules namely, Akt activation. However, incubation with stearate showed no such inhibitory effect (FIG. 2a). Decrease of insulin stimulation of IRS associated phosphorylation and IRS1 associated PI3 K activity by FFA has been reported earlier[13, 5, 20], here we show that palmitate alone can produce such defects. Another interesting trend observed in our study is the closeness of range of palmitate-induced inhibition. Densitometric analysis of Western blots indicates a two-fold decrease of insulin-stimulated phosphorylation of IRβ, PI3 K and Akt phosphorylation (data not shown). Neither insulin nor palmitate affected any alteration of protein profiles of IRβ, PI3 K and Akt (FIG. 2a). Our findings give an impression that palmitate disruption of insulin signals probably originates at IR level and the wave of inhibition then flows through the down stream signaling molecules. This restricts the recruitment of PI3 kinase resulting inhibition of $PIP_3$ association with Akt, which is expected to have adverse effect on Glut4 trafficking. Finally, a support in this direction was obtained with Glut4 translocation, which is essential for glucose entry into the cell. Insulin induced the translocation of GFP-Glut4 from the cytosol to the adipocyte membrane was totally inhibited by palmitate (FIG. 2b).

Figure 3A:
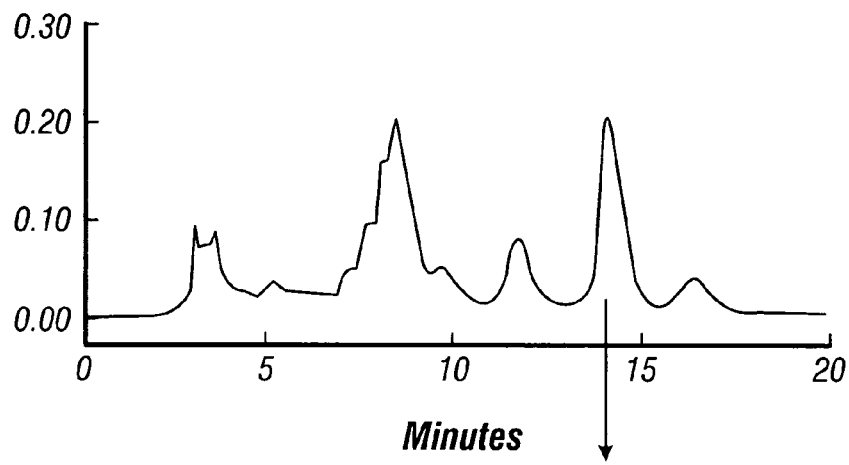
Figure 3A:
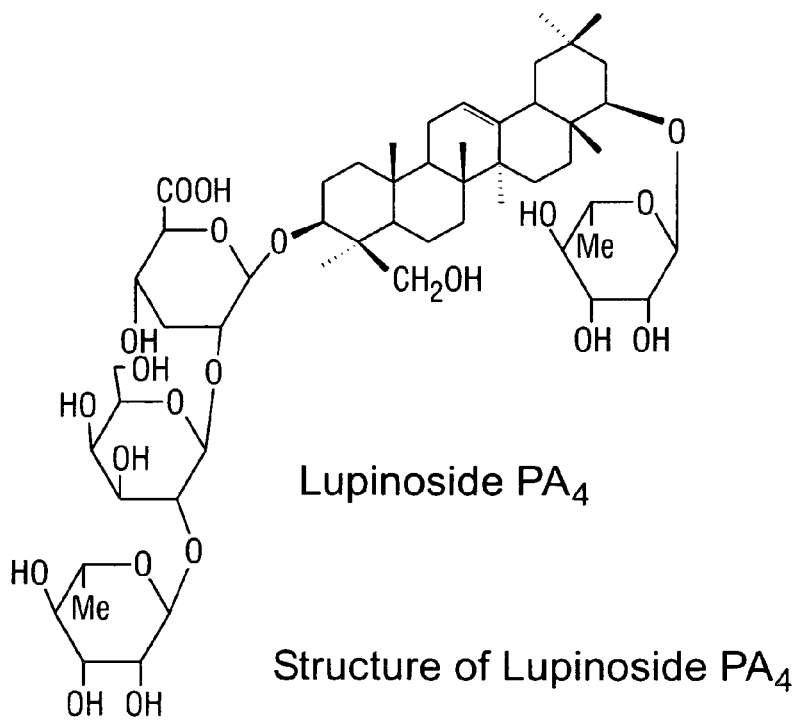
Figure 3B:
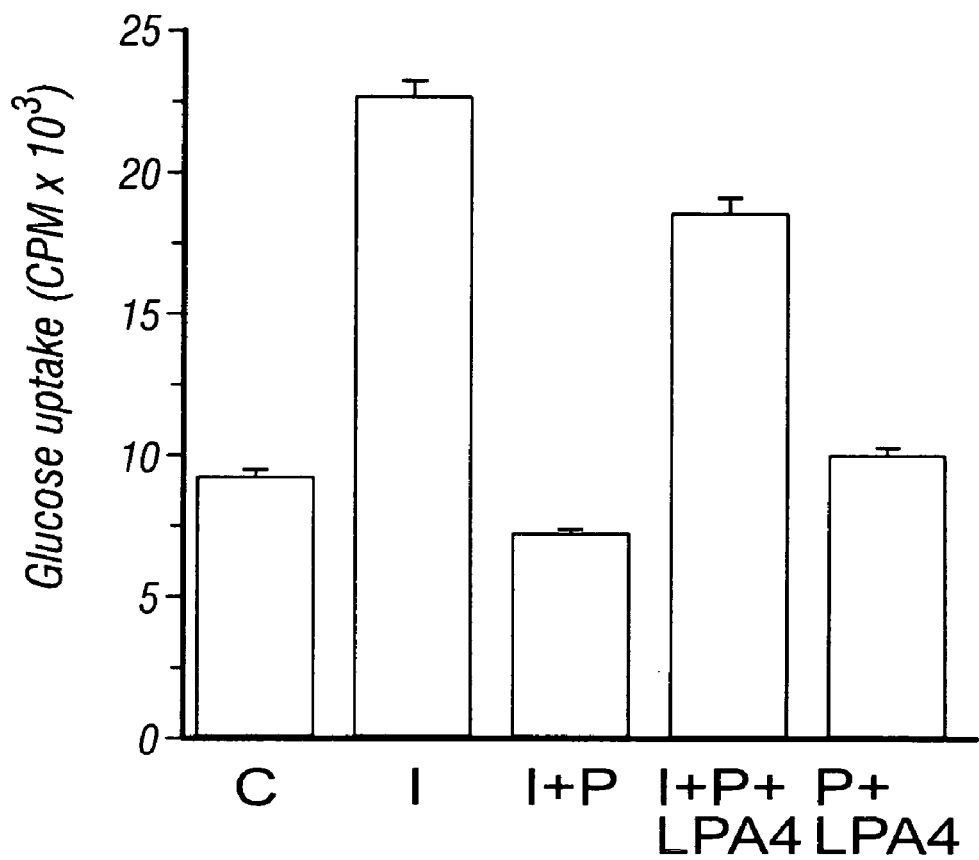
Figure 3C:
Figure 3C:
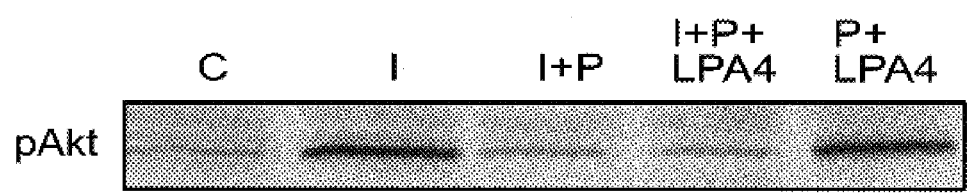

In the process of searching for anti-diabetic activity of medicinal plants of India, methanol-water (1:1) extract from *Pueraria tuberosa* root was found to improve palmitate impairment of insulin activity in terms of 3H-2DOG uptake by 3T3L1 cells. Using Diaion HP-20 chromatography, we obtained five fractions (A–E) of which fraction E showed required activity. Fractionation of E through Sephadex LH 20 chromatography yielded 3 fractions (F–H) where F showed improvement of palmitate induced damage. Fraction F was subsequently purified by HPLC to a single molecule, which was identified as Lupinoside PA432 by 2D NMR and mass spectrometry (FIG.3a). LPA4 protective property on the palmitate-induced impairment of insulin signaling molecules was then examined on 3T3L1 adipocytes. FIG. 3b demonstrates palmitate-induced reduction of insulin augmented 3H-2-DOG uptake by adipocyte could be prevented by LPA4. Attenuating effect of palmitate on insulin-stimulated IRβ tyrosine and Akt phosphorylation was waived by LPA4 (FIG. 3c).

Figure 3D:
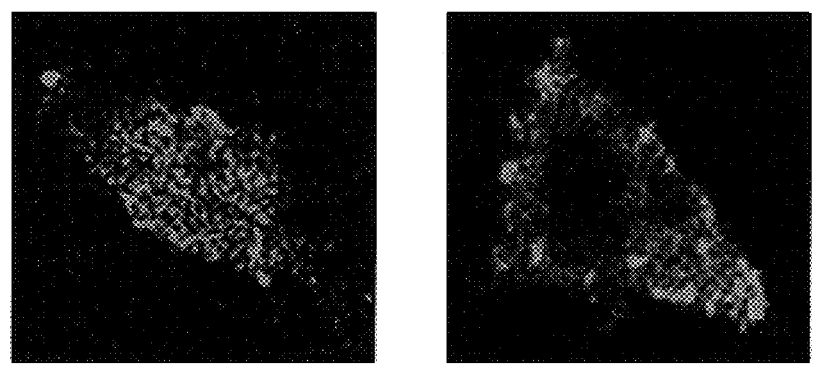
Figure 3D:
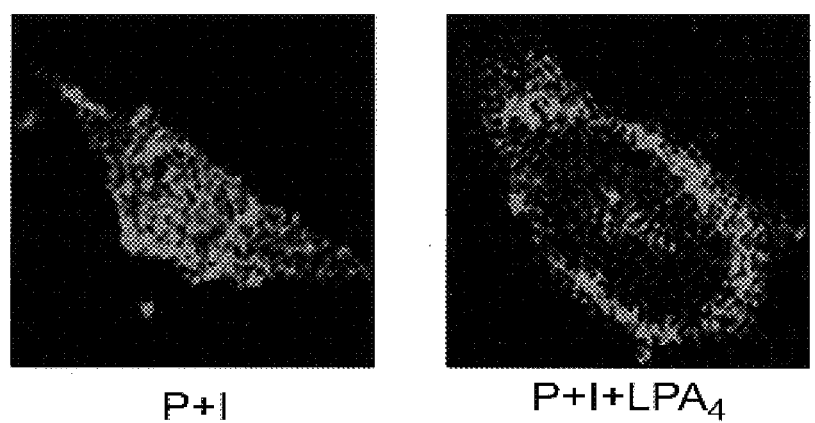

Akt is known to be a very important downstream signal, which activates Glut4, a process essential for its translocation to the plasma membrane in insulin target cells[33,34]. In response to insulin, Akt 2 is recruited to Glut4 containing vesicles and phosphorylates the component proteins[35]. Hence $LPA_4$ influence in waiving palmitate-induced inhibition of insulin stimulated Akt phosphorylation is meaningful, as damage in this pathway cause insulin resistance. This is further supported by our observation on palmitate inhibited insulin stimulation of Glut4 translocation. $LPA_4$ co-incubation with palmitate clearly permitted insulin stimulation of GFP-Glut4 translocation from cytoplasm to membrane (FIG. 3d). Glut4 is a vital transporter of glucose in insulin responsive cells, which constitutively recycles via the cell surface. Insulin actively sequesters Glut4 at an intracellular location that increase the rate of Glut4 trafficking to the membrane[33]. Although cellular mechanisms related to Glut4 trafficking events remain largely enigmatic but association of Glut4 translocation defects is involved in insulin resistance[34]. Our results with the determination of GFP-Glut4 translocation demonstrate complete block of insulin-stimulated Glut4 translocation by palmitate and that is totally withdrawn by $LPA_4$. These results are of particular interest in insulin resistance or diabetes type 2 for the following reasons: (i) Large number of studies implicates FFAs, particularly palmitate, in the development of insulin resistance[20-23]; (ii) Palmitate is the most abundant FFAs found in circulation and skeletal muscle cells[10,12]; (iii) one of the most prevalent acyl chains in diglyceride fraction of lipid extracts is palmitate[36]; (iv) consumption of palmitate decreases insulin sensitivity[37,38] and (v) insulin resistant muscles exhibit greater rates of palmitate uptake[39]. All these reports draw attention towards palmitate to be the major candidate among FFAs causing insulin resistance. However, a few studies indicate palmitate induced defects in insulin action is mediated by ceramide[12]. There may be number of pathways operative in insulin inaction, ceramide may be one of them and what we have observed is yet another, where palmitate is directly involved in causing insulin inaction. $LPA_4$ rescues insulin inactivation effected by palmitate. Since $LPA_4$ prevents insulin-signaling defects due to palmitate at all important steps including Glut4 translocation from cytoplasm to membrane, this lupinoside has encouraging possibilities as a therapeutic agent for insulin resistance and diabetes type 2.

DETAILED DESCRIPTION OF THE ACCOMPANYING DRAWINGS

The patent or application file contains at least one drawing executed in color. Copies of this patent or patent application publication with color drawing(s) will be provided by the Office upon request and payment of the necessary fee.

FIG. 1(a) Palmitate induced inhibition of insulin binding to receptor and receptor tyrosine kinase phosphorylation.

Autoradiograph of radiolabeled insulin and palmitate binding to solubilized insulin receptor preparations. 3T3 L1 adipocytes were incubated for 24 h without or with palmitate and receptor preparations were solubilized with 0.1% TritonX-100. 25 µg of protein was incubated overnight at 4° C. with 2 ng $^{125}$I-insulin (Specific activity 30.55 µCi/µg of protein). After termination of the incubation, it was pelleted by ultra centrifugation at $10^5$ g for 1 h. $^{125}$I-insulin was bound to the solubilized receptor preparation. Insulin receptor preparation and $^{125}$I-insulin was incubated in an identical manner in presence of cold palmitate (PA) or stearate (SA). 25 ug protein of solubilized receptor preparation was incubated overnight with [1-$^{14}$C]-palmitate at 4° C. and autoradiographed ($^{14}$C-PA).

FIG. 1(b) Determination of the binding affinity and receptor occupation by Scatchard analysis. $B_{max}$ and $K_a$ were calculated to be 7.3 pM and $0.16\times10^{10}M^{-1}$ respectively for insulin binding to solubilized receptor. But in the presence of palmitate, $K_a$ of insulin binding remained almost unchanged i.e. $0.158\times10^{10}M^{-1}$ but the $B_{max}$ was reduced to 3.46 pM.

FIG. 1(c) Panel i presents the homology model of the three domains (L1-Cys rich-L2) of the insulin receptor. The region on the L1 domain marked by the cyan band is the most probable insulin-binding site. Residues which on mutation to alanine reduced the binding constant by about 300 fold are coloured red; those which on mutation lowered the binding between 10 to 100 fold are coloured pink and the rest which reduced binding by 3 to 9 fold are coloured yellow. Cysteine residues are coloured green of which Cys-8 & Cys-26 (marked as ii within the red circle) and Cys-266 & Cys-274 (marked as iii within the red circle) are the most probable palmitoylation sites. Panels (ii) and (iii) show the electrostatic potential of the surroundings of the two probable pairs of cysteines, Cys-8 & Cys-26 and Cys-266 & Cys-274 which were selected as palmitoylation site for their dominant positive (blue) and neutral (white) electrostatic potential environment. Panel (iv) shows the electrostatic potential environment panel of Cys-192 & Cys-201, although it has right (positive and neutral) environment it was not selected as potential site as is fully buried under the surface. Panel (v) shows the electrostatic potential around Cys-126 & Cys-155 pair, which represents those discarded sites, which are predominantly negatively charged (red).

FIG. 1(d) Control and FFA treated 3T3L1 adipocytes were lysed by sonication in lysis buffer and centrifuged for 10 min at 10,000 g. 200 µg supernatant protein from control and treated cells was incubated overnight at 4° C. with 2 µg IRβ antibody. The antigen-antibody complex was pelleted with Protein A-agarose, pellets were washed thoroughly, resuspended and boiled in SDS-PAGE sample buffer and electrophoresed. Proteins from the gel were transferred to PVDF membrane and immunoblotted with anti-p-Tyr antibody. I-Insulin; P-palmitate; S-stearate.

FIG. 2(a) 3T3L1 adipocytes were incubated with palmitate and stearate as described in FIG. 1. On termination of incubation, cells were lysed by sonication in lysis buffer and centrifuged at 10,000 g for 10 min. Supernatant protein (50 µg each) was boiled for 5 min in SDS-PAGE sample buffer and resolved on 12% gel SDS-PAGE followed by transfer to PVDF membranes and immunodetected with p-IRS-1 (1:1000), p-PI3 kinase p 85 α (1:1000) and p-Akt 1/2 (1:1000) antibodies using alkaline phosphatase linked secondary antibodies. Anti-IRS 1, PI-3K and Akt 1/2 antibodies were used to detect the protein profiles due to treatments.

FIG. 2(b) Effect of palmitate on insulin induced Glut4 translocation in 3T3L1 adipocytes. 3T3L1 cells plated on coverslips were transfected for 48 h with GFP-Glut 4 plasmid (2 µg) using lipofectamine reagents. On stabilization, the cells were incubated in the absence or presence of palmitate for 24 h and then with insulin for 30 min. GFP-Glut 4 transfected cells incubated in the absence of fatty acids and insulin served as control (Con). After termination of incubation, localization of GFP-Glut 4 was examined using laser scanning confocal microscope.

FIG. 3(a) Structure and purification of $LPA_4$. Using Diaion HP-20 chromatography, obtained five fractions (A–E) of which fraction E showed required activity. Fractionation of E through Sephadex LH 20 chromatography yielded 3 fractions (F–H) where F showed improvement of paimitate induced impaired insulin activity. Fraction F was subsequently purified by HPLC to a single molecule, which was identified as Lupinoside $PA_4{}^{32}$ by 2D NMR and mass spectrometry FIG. 3(b) Adipocytes were treated for 24h in the presence of palmitate or palmitate plus $LPA_4$ or $LPA_4$ followed by 30 min insulin incubation. $^3$H-deoxyglucose was added to each incubation 5 min prior to the termination of incubation. Cells were then washed thrice with ice-cold KRP buffer in the presence of 0.3 mM phloretin to correct the glucose uptake data from simple diffusion and non-specific trapping of radioactivity. Cells were solubilized with 1% NP-40 and radioactivity was counted in a liquid scintillation counter.

FIG. 3(c) 3T3L1 adipocytes were incubated for 24 h in the absence or presence of palmitate or $LPA_4$ or palmitate plus $LPA_4$ and then with insulin 30 min. 50 µg of cell lysate in each case was subjected to denaturing gel and transferred to PVDF membrane and immunoblotted with anti-p-Akt antibody. 50 µg of cell lysate was immuno precipitated with anti-IRβ antibody and immunoblotted with anti-p-Tyr antibody.

FIG. 3(d) Glut 4 translocation of treated cells was determined in a similar manner as described under FIG. 2b.

METHODS

Cell Culture and treatments. 3T3-L1 cell line was procured from the National Centre for Cell Science, Pune, India and was cultured at 37° C. in 95%$O_2$/5% $CO_2$ in Dulbecco's Modified Eagle's Medium (DMEM) containing 25 mM glucose and 10% fetal calf serum. Confluent cells were treated, wherever mentioned, with 0.75 mM free fatty acids (FFAS; palmitate and stearate) for 24h.

Radiolabeled insulin binding to solubilized receptor preparations. Control and FFA treated 3T3L1 adipocytes were first washed thrice with 0.02M Phosphate Buffer (pH-7.4) containing 0.14M NaCl and then resuspended in Lysis Buffer (20 mM Tris-HCl, 40 mM NaCl, 5 mM EDTA, 5 mM Iodoacetamide, pH-8.4) supplemented with protease inhibitors (1 µg/ml aprotinin, 1 µg/ml pepstatin, 1 µg/ml leupeptin, 2 mM phenyl methyl sulfonyl fluoride and 1 µg/ml trypsin inhibitor). These cells were then freeze thawed thrice at –70° C. and centrifuged at 10,000 rpm for 15 min at 4° C. The pellet collected was resuspended in Lysis Buffer, sonicated and again centrifuged at 10,000 rpm for 15–20 min at 4° C. The supernatant was dialysed overnight against 10 mM Tris-HCl (pH-7.4) buffer and volume reduced by lyophilisation. The membrane preparation was then mixed with 0.1M lithium diiodosalicylate to a membrane protein concentration of approximately 5 mg/ml and the mixture was homogenised in a motor driven glass-Teflon tissue homogenizer, it was centrifuged at 35,000 g for 20 min and supernatant was dialysed for 12 hours against 20 mM sodium bicarbonate, pH-9.4. To this solution 0.1%

TritonX-100 (v/v) and 25% glycerol was added with constant stirring. The solution was lyophilised to reduce the volume and subjected to dialysis against 10 mM Tris-HCl buffer (pH-8.4).

Recombinant human insulin was radiolabelled with $^{125}$I and $^{125}$I-insulin was separated from free iodine by using Sephadex-G15 column equilibrated with 0.01M Phosphate Buffer (pH-7.2) containing 0.14M NaCl and 1% (w/v) BSA. Specific activity of $^{125}$I-insulin was 30.55 µCi/µg of protein.

Solubilized insulin receptor preparation from control and FFA treated 3T3L1 adipocytes (25 µg for each incubation) was incubated overnight at 4° C. with 2 ng $^{125}$I labeled recombinant human insulin in a final volume of 500 µl of 0.02M Phosphate Buffer (pH-8.4) containing 0.15M NaCl and 0.25% BSA (PBS). On termination of incubation, it was pelleted by ultracentrifugation (Sorvall Ultra-80) at $10^5$ g for 1 hour. Pellet in each tube was dissolved in 1× sample buffer (63 mM Tris HCl pH 6.8, 10% glycerol, 2% SDS, and 0.025% Bromophenol blue) and subjected to non-denaturing SDS-PAGE (4% stacking gel was layered on the top of a 6.5% resolving gel). The gel was dried, exposed to Kodak X-OMAT AR and autoradiographed (see FIG. 1a).

Scatchard Analysis. To determine the optimum binding conditions of $^{125}$I-Insulin to the receptor protein, binding incubations were performed at different temperatures and time intervals with varied amount of solubilized receptor preparations. It was found that overnight incubation at pH 8.4 and a temperature of 4° C. permitted maximum radiolabeled insulin binding. The receptor preparations (15 µg protein) was incubated overnight at 4° C. in a final volume of 500 µl buffer (0.02M Phosphate Buffer, pH 8.4, containing 0.15M NaCl and 0.25% BSA) with varying concentrations of $^{125}$I-Insulin (0.18–0.72 nmoles/L) in the absence (total binding) or presence of 10,000fold excess unlabeled insulin (non-specific binding). In another set of experiment receptor preparation was incubated simultaneously with $^{125}$I-Insulin and unlabeled insulin except the presence of 0.08 mM of unlabeled palmitate. After the termination of the incubations, free and bound radioactivity was separated by the addition of 500 µl of 0.5% chilled polyethylene glycol (PEG; MW 6000). The samples were mixed thoroughly by vortexing and kept under ice for 10 min and followed by centrifugation at 20,000 g in a refrigerated centrifuge for 15 min. The supernatant was aspirated out and the pellet was washed three times with washing buffer (0.02M Phosphate Buffer containing 0.15M NaCl and 0.25% BSA). The radioactivity in the final pellet was measured in a $^{125}$I-gamma counter. The specific binding was calculated by subtracting non-specific binding from total binding. Data were then analyzed by Scatchard analysis to determine the affinity and capacity of insulin receptor binding in the presence or absence of palmitic acid (see FIG. 1b).

Molecular modeling. The homology model of the insulin receptor was done on the x-ray structure (PDB1 IGR.ENT, with amino acid identity of 59%) of IGF-1 R$^{27}$ using InsightII 98.0 (Accelrys Inc., San Diego, Calif., USA). Energy minimization and molecular dynamics were performed with the DISCOVER module of Insightil using cff91 forcefield on a Silicon Graphics$^R$ OCTANE workstation. Energy minimizations were done with a convergence criterion of 0.001 kcal/mol, using a combination of steepest descent and conjugate gradient methods (100 steps each); these steps were repeated until satisfactory conformational parameters were obtained. Molecular dynamics simulations were carried out using a time step of 1 fempto second for 100 steps of equilibration and 1000 steps of dynamics. Distance constraints were applied to the other parts of the molecule while running minimization and dynamics for regularization of selected segments (see FIG. 1c).

Immunoprecipitation. 200 µg of control and FFA treated cell lysates (sonicated in ice for 10 min in lysis buffer [1% NP-40, 20 mM HEPES (pH 7.4), 2 mM EDTA, 100 mM NaF, 10 mM sodium pyrophosphate, 1 mM sodium orthovanadate, 1 µg/ml leupeptin, 1 µg/ml aprotinin, 1 µg/ml pepstatin and 1 mM PMSF] followed by) were incubated overnight at 4° C. with 2 µg insulin receptor (IR) β antibody. 50 µl of Protein A-agarose was added to each tube and incubated at 4° C. for 2 h. After centrifugation at 10,000 g for 2 min at 4° C., 500 µl of 0.1% CHAPS in PBS was added to the pellets, resuspended and centrifuged at 10,000 g at 4° C. for 2 min. The pellets were washed thoroughly and subjected SDS-PAGE followed by Western Blot using anti-phosphotyrosine antibody (anti-mouse; 1:1000) (see FIG. 1d).

Electrophoresis and Immunoblotting. Control and treated cell lysates (60 µg) were resolved on 10% SDS-PAGE and transferred to PVDF membranes (Millipore, Bedford, Mass. 01730) in transfer buffer (25 mM Tris, 193 mm glycine, 20% methanol, pH 8.5) for 1.5 h at 4° C. at 90 V. Membranes were blocked with 5% non-fat dried milk in TBST buffer (20 mM Tris base, 137 mM NaCl, 1 mM HCl, 0.1% Tween 20) and incubated overnight with anti p-IRS (anti-goat; 1:1000), anti p-PI3K (anti-goat; 1:1000) and anti p-Akt (anti-rabbit; 1:2000). Immunoreactive bands were detected with alkaline phosphatase linked secondary antibodies (see FIG. 2a).

Transfection and Glut 4 translocation. 3T3L1 Cells were plated on 60 mm plate containing coverslips and maintained in an air/$CO_2$ (19:1) atmosphere in DMEM supplemented with 10% (v/v) FBS and 100 µg/ml penicillin/streptomycin. After 24 hrs, cells were washed with DMEM free from FBS and antibiotics. Plasmid DNA of GFP-Glut4 (2 µg) was used to transfect $2\times10^5$ cells on each 60 mm plate with Lipofectamine reagent in accordance with the manufacturer's protocol (Life Technologies). After 48 h of transfection, cells were treated without or with 0.75 mM palmitate for 24 h and then incubated for 30 min in the absence or presence of 100 nM insulin. Cells on the coverslips were fixed in paraformaldehyde (3.5%) and mounted on to glass slides. The coverslips were examined for translocation of GFP-Glut 4 under laser scanning confocal microscope (Leica Corp., Rockleigh, N.J.) (see FIG. 2b).

Extraction and Isolation of Lupinoside PA$_4$ from *Pueraria tuberosa*:

*Pueraria tuberosa* root (1 kg was cut finely and extracted with methanol (3×1.5 L). The extracted solution, after evaporation in vacuo, gave a residue (90 g) and was evaluated for bioactivity. The methanol extract was partitioned between ethyl acetate and water. The aqueous layer was further extracted with n-butanol. Removal of the solvent in vacuo from ethyl acetate-soluble portion, n-butanol-soluble portion and aqueous phase yielded 2.5 g, 12 g, and 64 g of fraction respectively. Each fraction was tested for bioactivity and activity was found in n-butanol fraction. This fraction was subjected to Diaion HP-20 chromatography with water and methanol as eluent. The methanol eluent was evaporated to dryness (2.4 g) and was further subjected to Sephadex LH-20 chromatography using methanol-water (1:1) and methanol as fluent. Evaporation of methanol-water fraction under reduced pressure yielded a solid (1.4 g) that showed biological activity. Preparative HPLC (µ-Bondapak, C-18 reverse phase column, methanol-1% aqueous acetic acid (7:3), flow 12 mm/min and UV as detector as 210 nm) of this solid furnished a homogeneous compound identified as lupinoside $PA_4$ (L $PA_4$)[32] (0.28 g) whose structure was determined by 1D, 2D NMR and Q-TOF-MS and some chemical reactions (see FIG. 3a).

Effect of $LPA_4$ treatment on palmitate induced inhibition of glucose uptake. 3T3L1 adipocytes were treated for 24 h in the absence and presence of $LPA_4$ (20 μg/ml) and palmitate (0.75 mM) followed by 30 min incubation with 100 nM insulin in Kreb's Ringer Phosphate (KRP) buffer (12.5 mM HEPES, pH 7.4, 120 mM NaCl, 6 mM KCl, 1.2 mM $MgSO_4$, 1 mM $CaCl_2$, 0.4 mM $NaH_2PO_4$, 0.6 mM $Na_2HPO_4$) supplemented with 0.2% bovine serum albumin and then $^3$H-2-DOG (0.4 nmoles) was added to each incubation 5 min prior to the termination of incubation. 3T3L1 cells were washed thrice with ice-cold KRP buffer in the presence of 0.3 mM phloretin to correct the glucose uptake data from simple diffusion and non specific trapping of radioactivity. Cells were solubilized with 1% NP-40 and [$^3$H]-deoxyglucose was measured in a Liquid Scintillation counter (Packard, Tricarb 2100 TR) (see FIG. 3b).

3T3L1 cells incubated in an identical manner in the absence or presence of $LPA_4$ and palmitate were lysed by sonication and lysates were detected for p-IR and p-Akt as described above (see FIG. 3c). In another set of experiment cells were transfected with GFP-Glut4 as described above followed by incubation without or with $LPA_4$ and palmitate for 24 h. Cells were then incubated with 100 nM insulin and Glut4 translocation was monitored under a confocal microscope (see FIG. 3d).

What is claimed is:

1. An in vitro method of preventing and/or reducing the risk of development of type 2 diabetes, said method comprising a step of administering a pharmaceutically effective amount of a root extract of plant *Pueraria tuberosa* or butanol fraction of the extract or Lupinoside $A_4$ ($LPA_4$), optionally along with additive(s) to cells.

2. A method as claimed in claim 1, wherein said method of preventing and/or reducing the risk of develonment of type 2 diabetes is by means of augmenting glucose transporter-4 (Glut4) phosphorylation and Glut4 translocation to enhance insulin signal in a signal transduction pathway.

3. A method as claimed in claim 1, wherein the extract is an aqueous extract.

4. A method as claimed in claim 1, wherein the additive(s), is proteins, carbohydrates, sugars, talc, magnesium, stearate, cellulose, calcium carbonate, starch, gelatin paste, pharmaceutically acceptable carriers, excipients, diluents, and/or, solvent.

5. A method as claimed in claim 1, wherein said method shows an increase in glucose uptake by the cells.

6. A method as claimed in claim 1, wherein said method is nontoxic to said cells.

7. A method as claimed in claim 1, wherein said extract prevents palmitate induced defects on insulin signaling.

* * * * *